(12) United States Patent
Nam et al.

(10) Patent No.: US 9,559,360 B2
(45) Date of Patent: *Jan. 31, 2017

(54) VIRUS SCAFFOLD FOR SELF-ASSEMBLED, FLEXIBLE AND LIGHT LITHIUM BATTERY

(75) Inventors: Ki Tae Nam, Cambridge, MA (US); Chung-Yi Chiang, Cambridge, MA (US); Angela M. Belcher, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 140 days.

This patent is subject to a terminal disclaimer.

(21) Appl. No.: 13/431,151

(22) Filed: Mar. 27, 2012

(65) Prior Publication Data

US 2012/0178145 A1    Jul. 12, 2012

Related U.S. Application Data

(63) Continuation of application No. 11/254,540, filed on Oct. 19, 2005, now Pat. No. 8,283,325.

(60) Provisional application No. 60/620,522, filed on Oct. 19, 2004.

(51) Int. Cl.
| | |
|---|---|
| *H01M 4/62* | (2006.01) |
| *H01M 8/16* | (2006.01) |
| *C07K 4/02* | (2006.01) |
| *H01B 1/12* | (2006.01) |
| *H01M 4/133* | (2010.01) |
| *H01M 4/485* | (2010.01) |
| *H01M 4/587* | (2010.01) |
| *H01M 4/60* | (2006.01) |
| *H01M 10/0525* | (2010.01) |
| *H01M 4/02* | (2006.01) |

(52) U.S. Cl.
CPC ............. *H01M 4/62* (2013.01); *C07K 4/02* (2013.01); *H01B 1/122* (2013.01); *H01M 4/133* (2013.01); *H01M 4/485* (2013.01); *H01M 4/587* (2013.01); *H01M 4/60* (2013.01); *H01M 8/16* (2013.01); *H01M 10/0525* (2013.01); *H01M 2004/021* (2013.01); *Y02E 60/122* (2013.01)

(58) Field of Classification Search
None
See application file for complete search history.

(56) References Cited

U.S. PATENT DOCUMENTS

| | | | |
|---|---|---|---|
| 5,569,745 A | 10/1996 | Goodbody et al. | |
| 5,595,839 A | 1/1997 | Hossain | |
| 8,283,325 B2 * | 10/2012 | Nam et al. | 514/21.8 |
| 2003/0044893 A1 * | 3/2003 | Baum et al. | 435/69.1 |
| 2006/0172282 A1 | 8/2006 | Naik et al. | |

FOREIGN PATENT DOCUMENTS

| | | |
|---|---|---|
| WO | WO 03/078451 A2 | 9/2003 |
| WO | WO 2005/037856 A2 | 4/2005 |
| WO | WO 2005/049073 * | 6/2005 |

OTHER PUBLICATIONS

Hundley et al ('Electrolytic reduction of cobalt in ammoniacal leach solutions' Bureau of Mines Report of Investigations, 1985 pp. 1-20).*
Bala et al ('Interaction of different metal ions with carboxylic acid group: a quantitative study' J. Phys. Chem. A v111 2007 pp. 6183-6190).*
Mizoguchi et al ('Nectin: an adhesion molecule involved in formation of synapses' The Journal of Cell Biology v156(3) Feb. 4, 2002 pp. 555-565).*
Boal et al ('Microtubule template synthesis of inorganic nanomaterials' Mat Res Soc Symp Proc v823 2004 pp. w4.3.1-w4.3.6).*
Mat Res Soc proceedings library (Table of contents for Jan. 2004 vol. 283, 4 pages).*
Tubulin sequence (retrieved from http://www.ncbi.nlm.nih.gov/protein/114052731?report=genbank&log$=protalign&blast_rank=15&RID=EJAMPX16015 on Jan. 29, 2014, 2 pages).*
Wolschin et al ('Enrichment of phosphorylated proteins and peptides from complex mixtures using metal oxide/hydroxide affinity chromatography (MOAC)' Proteomics v5 2005 pp. 4389-4397).*
Proteomics table of contents (retrieved from http://onlinelibrary.wiley.com/doi/10.1002/pmic.v5:17/issuetoc on Jan. 29, 2014, 10 pages).*
Periodic Table of Elements: LANL (Los Alamos National Laboratory), Accessed on Feb. 10, 2014 at http://periodic.lanl.gov/index.shtml, 1 page.*
Arabidopsis thaliana protein NP_179763 (retrieved from http://www.ncbi.nlm.nih.gov/protein/186502112?report=genbank&log$=prottop&blast_ra on Jun. 25, 2014, 2 pages).*
Arabidopsis thaliana protein NP_179763 phosphorylation (retrieved from http://www.cbs.dtu.dk/cgi-bin/webface2.fcgi?jobid=53AB082F0000662237719483&wait= on Jun. 25, 2014, 3 pages).*
Naim et al ('Mechanism of adjuvancy: I-metal oxides as adjuvants' Vaccine v15(11) 1997 pp. 1183-1193).*
Definition of include (retrieved from http://www.oxforddictionaries.com/us/definition/american_english/include on Feb. 29, 2016, 11 pages).*
Pubchem entry for aluminum oxide (retrieved from https://pubchem.ncbi.nlm.nih.gov/compound/aluminum_oxide on Mar. 1, 2016, 51 pages).*
Mao et al., "Virus-based toolkit for the directed synthesis of magnetic and semiconducting nanowires," Science, vol. 303 (2004) pp. 213-217.
Carswell ('Virus battery' Sciencentral archive dated Sep. 22, 2005 retrieved from http://www.sciencentral.com/articles/view.php3?article_id=2183292647 on Aug. 16, 2011, 2 pages).
Yoo et al., ('Two-dimensional self-assembly of engineered M13 virus on polyelectrolyte multiplayer' ACS National Meeting dated Aug. 30, 2005 retrieved from http://oasys2.confex.com/acs/230nm/techprogram/P891728.HTM on Aug. 16, 2011, 1 page).

(Continued)

*Primary Examiner* — Karlheinz R Skowronek
*Assistant Examiner* — Ronald Niebauer
(74) *Attorney, Agent, or Firm* — Foley & Lardner LLP

(57) ABSTRACT

A variety of compositions that include a metal oxide, films and batteries comprising one or more of the compositions, and methods of making the same.

20 Claims, 4 Drawing Sheets

(56) References Cited

OTHER PUBLICATIONS

Chen et al. ('Probing the interaction between peptides and metal oxides using point mutants of a TiO2 binding peptide' Langmuir v24 2008 pp. 6852-6857).
Poizot et al. (Nature 2000 v407 pp. 496-499).
Mao et al. (PNAS 2003 v100 pp. 6946-6951).

\* cited by examiner

VIRUS SCAFFOLD FOR SELF-ASSEMBLED, FLEXIBLE AND LIGHT LITHIUM BATTERY

This application is a Continuation of U.S. application Ser. No. 11/254,540, filed Oct. 19, 2005, which claims priority to U.S. Provisional Application No. 60/620,522, filed Oct. 19, 2004, the entire contents of which are incorporated herein by reference.

The instant application contains a Sequence Listing which has been submitted in ASCII format via EFS-WEB and is hereby incorporated by reference in its entirety. Said ASCII copy, created on Mar. 21, 20121, is named sequence.txt and is 1 KB.

FIELD OF THE INVENTION

This invention pertains to production of electrodes for rechargeable lithium-ion batteries using a biological template.

BACKGROUND OF THE INVENTION

The increasing demand for portable devices is driving the development of small, rechargeable batteries with high energy density. Lithium-ion batteries are the system of choice owing to their higher specific energy (100-150 Wh/kg), higher specific power (150-250 W/kg) and longer lifespan (>1000 cycles) in comparison to other types of batteries. These advantages result from the battery's high voltage (2.4-4.6 V) and the high theoretical capacity density of the lithium carrier ion (3862 Ah/kg). The performance of a lithium-ion battery is heavily influenced by the intercalation materials used in its anode and cathode. (1) The intrinsic properties of the intercalation material determine the cell's voltage, capacity, and stability, which in turn determines the individual cycle-life and total lifetime of the battery.

Carbonaceous compounds (e.g., graphite and coke) have been widely used as anode materials in lithium-ion batteries because their electrochemical potentials are similar to that of lithium metal and because, unlike lithium metal anodes, they do not form dendrites. Most of the known lithium/transition metal oxides [LiMO2 (M: Co, Fe, Mn, Ni)] and nanotubes, for example carbon and TiO2 nanotubes, (2,3) have been studied for use as cathode materials.

Layered lithium nickel dioxide (LiNiO2) was one of the first lithium-metal oxides considered (4) as a cathode material because of its favorable specific capacity. However, it was found that the layered crystalline structure of delithiated $Li_xNiO_2$ would collapse after the exothermic oxidation of the organic electrolyte. The collapse of the layered structure results in accumulation of lithium atoms on the electrode/electrolyte interface. The accumulated lithium atoms form dendrites, which penetrate the separators and create a short circuit inside the battery that can cause an explosion. On the other hand, the crystalline structure of delithiated lithium cobalt dioxide ($Li_xCoO_2$) is more stable than that of $Li_x$-$NiO_2$. $LiCoO_2$ is widely used in commercial lithium-ion batteries; however, the capacity of $Li_xCoO_2$ (~150 mAh/g) is smaller than that of $Li_xNiO_2$ (~250 mAh/g).

To improve the capacity and stability of intercalation materials, several routes have been investigated. For example, lithium-metal oxides have been doped with inert di-, tri- or tetravalent cationic elements (e.g. Ti and Mg). These elements substitute for Ni or Co and stabilize the layered structure of the intercalation materials. However, this $LiM_{1-x}Ti_{x/2}Mg_{x/2}O_2$ (M:Co or Ni) phase (5) is difficult to synthesize. Another approach employs chimie douce (soft chemistry) to synthesize the layered lithium manganese dioxide ($LiMnO_2$) phase. However, the layered phase is structurally unstable and transitions to an unstable spinel, $Li_xMn_2O_4$, during use. (6) While electrochemically attractive, these materials exhibit limited cycling life and storage capacity.

Tuning the morphology or texture of lithium-intercalated materials to produce porous, high surface area composites presents an alternative strategy for improving electrode capacities and stabilities. For example, electrodes fabricated from mesoporous vanadium oxide ($V_2O_5$) were reported to have capacities up to 100% greater than electrodes of polycrystalline non-porous $V_2O_5$ powder. (7)

Still, it is desirable to have an electrode material for lithium ion batteries that exhibits improved capacity and stability.

SUMMARY OF THE INVENTION

The present invention provides a variety of compositions that include a metal oxide, films and batteries comprising one or more of the compositions, and methods of making the same.

In one aspect, the invention provides a metal oxide coordinated to a first peptide, the first peptide exhibiting an affinity for a reduced form of the metal. In certain embodiments of the invention the metal comprises a transition metal, e.g., cobalt, vanadium, nickel, manganese, iron, cadmium, tungsten, chromium, zirconium, titanium, scandium, yttrium, copper, calcium, aluminum, barium, beryllium, magnesium, and strontium. In certain embodiments of the invention the metal oxide is an oxidized metal nanoparticle. In certain embodiments of the invention the metal oxide can intercalate lithium ions.

In certain embodiments of the invention the first peptide includes carboxylated amino acids. In a particular embodiment the sequence of the first peptide is AEEEED (SEQ ID: 1) and the metal is cobalt. The peptide may be part of a virus.

In certain aspects of the invention, the composition further includes a second peptide that selectively binds a predetermined metal selected from copper, nickel, gold, silver, platinum, and palladium. In a particular embodiment of these aspects of the invention the sequence of the second peptide may be LKAHLPPSRLPS (SEQ ID: 2) and the predetermined metal may be gold.

The composition that includes a second peptide that selectively binds a predetermined metal may further comprise the predetermined metal. The predetermined metal may be, e.g., between about 1% and about 30% of the metal coordinated to a protein coat of the virus. In some embodiments the predetermined metal is between about 15% and about 30% of the metal coordinated to a protein coat of the virus. In certain embodiments of the invention a first portion of a predetermined coat protein on the virus includes the first peptide, and a second portion of the predetermined coat protein includes the second peptide. The first peptide may be part of a first predetermined coat protein, and the second peptide may be part of a second predetermined coat protein.

In another aspect, the invention provides a composition produced by steps that include: (i) providing a first peptide exhibiting an affinity for metal ions; (ii) coordinating a metal to the first peptide; and (iii) oxidizing the coordinated metal to form a crystallite of the metal oxide. In certain embodiments of the invention the crystallite has a size between 2 nm and 1000 nm. In certain embodiments of this aspect of the invention, providing a first peptide includees providing a population of virus displaying the first peptide. The invention further provides the foregoing composition, wherein substantially all the virus is removed from the composition.

In another aspect, the invention provides a film that includes any of the afore-mentioned compositions. The film may, e.g., exhibit long range order or short range order. In certain embodiments of the invention the film does not exhibit long range order. In certain embodiments of the invention the film does not exhibit short range order. The film may be between about 10 nm and about 10 μm thick.

In another aspect, the invention provides a lithium ion battery that includes: (i) an electrolyte; and (ii) a lithium accumulation layer disposed adjacent to the electrolyte, the lithium accumulation layer that includes any of the afore-mentioned compositions. The battery may further include an electrode material adjacent to the lithium accumulation layer, wherein the lithium accumulation layer is disposed between the electrode material and the electrolyte. The electrolyte may be a solid or a fluid.

In another aspect, the invention provides a method of producing a thin film, the method including steps of: (i) providing a plurality of nanotubes, the nanotubes comprising a virus to which a metal oxide is coordinated; and (ii) casting the plurality into a film. In certain embodiments of this method, providing a plurality of nanotubes includes: (i) providing a population of virus comprising a first peptide exhibiting an affinity for metals; (ii) coordinating a metal to the first peptide; and (iii) oxidizing the coordinated metal to form a crystallite of the metal oxide disposed about the virus.

BRIEF DESCRIPTION OF THE DRAWING

The invention is described with reference to the several figures of the drawing, in which.

DETAILED DESCRIPTION OF CERTAIN PREFERRED EMBODIMENTS

Figure 1:
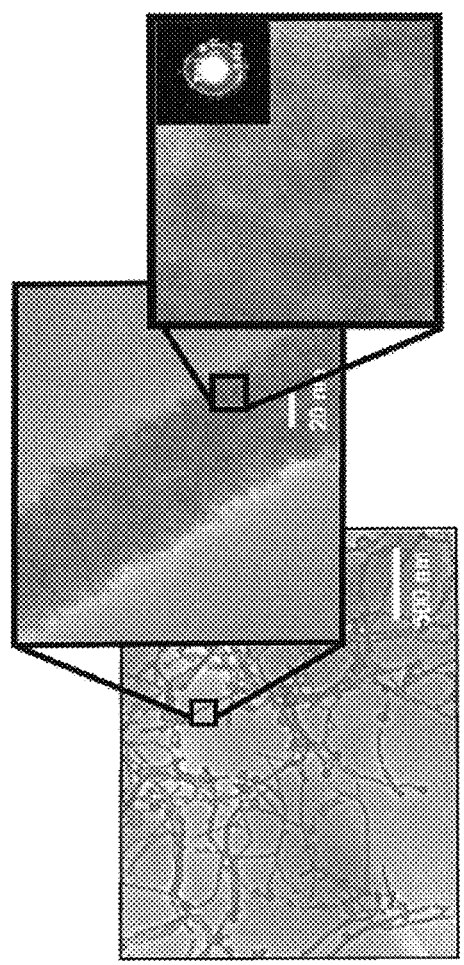
FIG. 1 is a transmission electron microscopy image of virus-based $Co_3O_4$ nanotubes.

M13 bacteriophage contains about 2700 copies of a major coat protein, pVIII protein, which are longitudinally assembled along the virus's DNA. Moreover, several copies of minor coat proteins (pIII, pVI, pVII, and pIX proteins) are assembled at the two ends of the virus. This unique periodic, uniform structure is genetically controlled. Therefore, we can use this particular property of M13 bacteriophage to create tailor-made nanostructure electrode materials that exhibit improved structural stability and higher capacity.

In one embodiment, the major coat protein of M13 bacteriophage is genetically engineered to specifically bind to metal ions or nanoparticles. Metal oxide nanotubes are synthesized using this engineered virus template. Due to the anisotropic structure of bacteriophage, the virus-based metal oxide nanotubes self-assemble into a mesoporous nanocrystalline film. Intercalation of lithium through and between the virus-based nanotubes, as well as their high specific surface area, can greatly increase the capacity of the films for lithium ions. Furthermore, the highly oriented helical major coat proteins of M13 virus promote the structural stability of individual virus-based nanotubes, increasing the total life of lithium-ion batteries incorporating them. Other viruses, such as f1, fd, and tobacco mosaic virus (TMV) may also be employed in embodiments of the invention.

Mesoporous Thin Films for Lithium Ion Batteries

Films produced using virus based metal/oxide nanotubes according to an embodiment of the invention may be used in all parts of a lithium-ion battery. A lithium-ion battery employs lithium ions as a charge carrier in the battery, completing the circuit traversed by electrons circulating from the battery to a load. In some prior art batteries, lithium ions are inserted in intercalation layers, e.g., graphite layers, in the anode of the battery. As the battery discharges, the lithium ions leave the cathode and traverse the electrolyte to the anode. When the battery is charged, the lithium ions leave the anode and travel back across the electrolyte to the cathode.

The stability of the crystalline microstructure of the electrodes determines the lifespan of a lithium-ion battery. The long-range order of virus-based nanotubes and the stiffness of bacteriophage itself provide good mechanical properties to virus-based films. In addition, both the proteins and the nanotubes themselves stabilize virus-based thin films against fatigue. As discussed above, delithiated lithium-transition metal oxides may collapse. The intercalation of lithium ions in metal oxides causes them to expand; diffusion of the lithium ions out of the oxide during the reverse cycle allows the expanded oxide to relax and contract. This repeated volume change can cause a solid oxide material to crack.

In contrast, because the nanotubes are not affixed to one another, they can shift within the film to accommodate lithium ions that are incorporated into the cathode film during battery discharge and to accommodate the volume change resulting from the ejection of those lithium ions as the battery is charged. Likewise, the flexible protein chains in the virus coat can also shift to accommodate lithium ions in the cathode film without causing permanent cracks in the nanotube. In addition, the flexibility of the proteins and the malleability of the film may also promote diffusion of the lithium ions through the film. The highly oriented helical major proteins of M13 can stabilize the microstructure because of the layered crystalline structure regulated by the proteins and their strong binding affinity for metal oxides.

Synthesis of a Virus-Based Metal Oxide Nanotube.

M13 is a filamentous phage (~880 nm long and 6 nm in diameter) whose capsid includes several proteins (pI-pVIII). At one end of the M13 virus, there are approximately five copies each of pII and pIX. The other end has about five copies each of pill and pVI. The wild-type M13 virus coat includes about 2700 copies of major coat protein pVIII, which are stacked in units of five in a helical array. The various proteins may be genetically modified to have a specific peptide motif that can bind and organize nanomaterials. Because the amino acid sequence of this motif is genetically linked to the virus DNA and contained within the virus capsid, exact genetic copies of the virus scaffold can be created easily and quickly reproduced by infection into bacterial hosts. In one embodiment, glutamic acid and aspartic acid, which contain carboxylic acid sidechains, are genetically expressed in the pVIII protein and used to bind various metal ions via chelation. An exemplary peptide sequence is AEEEED (SEQ ID:1) ("sequence E4") Longer sequences, including 5 to 25 amino acids or more, for example, 5 to 10, 10 to 15, 15-20, or 20-25 amino acids, may also be employed. The terminal amino acids on either end of the peptide may be carboxylated or not; however, it may be preferable that the peptide not include amino acids that would interfere with the interaction of the peptide and the metal. The ratio of glutamate to aspartate in the peptides may range from 100% glutamate to 100% aspartate. Alternatively or in addition, an inert peptide sequence may be coupled to the carboxylated peptide sequence, or a peptide that is selective for some other material may be coupled to the carboxylated peptide. The carboxylate enhancement may be expressed on all the pVIII chains (100% display) or may be partially displayed using various techniques for modifying bacteriophage genomes well known to those skilled in the art. (9) Alternatively or in addition, the carboxylate enhancement may be expressed on one of the other coat proteins, e.g., pIII.

Variation of the degree of carboxylate expression may modify the conformation and crystalline structure of the virus-based nanotubes. In addition, variation of the number of carboxylate groups or different mixtures of aspartic acid and glutamic acid residues may also influence the microstructure of the oxide. The affinity of the desired metal or its oxide for the modified virus may be optimized using the phage display library techniques described in US20030073104, published Apr. 17, 2003, the contents of which are incorporated herein by reference. Phage display is a combinatorial technique in which a 'random library' of viruses is exposed to a substrate of interest. In some embodiments, the random library includes roughly $10^{11}$ viruses that have each been uniquely modified, representing about $10^9$ variations. The modification may take the form of an additional amino acid sequence which is expressed on one of the coat proteins of the viral assembly. Peptides containing various amounts of carboxylate and ratios of aspartate and glutamate may be tested for their affinity to a metal or oxide surface.

As used herein, the term "peptide" denotes a string of at least two amino acids linked together by peptide bonds. Peptide may refer to an individual peptide or a collection of peptides. Peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired activity of the peptide.

Lithium ion batteries often exhibit a decay in voltage after repeated recharging cycles. This reduces the lifetime of the battery, as the capacity of the battery may not provide a reasonable battery life or sufficient power after a certain number of charges. One possible contributor to this effect is the irreversible binding of lithium ions to each other and to impurities at the cathode and anode of the battery. In some batteries, a solid electrolyte interface is disposed between the electrode, especially graphite anodes, and the electrolyte to prevent migration of the lithium ions to the electrode. Where the ions do not migrate all the way to the electrode, the circuit may be maintained by conducting electrons from the electrode to a solid electrolyte interface material.

The use of phage display provides a method to co-locate both ionic and electronic conductors. In one embodiment, a peptide sequence that selectively binds an electronic conductor may be incorporated into the protein coat of the virus. For example, biopanning may be used to identify a peptide sequence that is selective for a desired catalyst, e.g., copper, gold, silver, nickel, platinum, palladium, etc. An exemplary peptide that selectively binds gold is LKAHLPPSRLPS (SEQ ID:2). This peptide may be expressed on a different coat protein than the modified coat protein that binds the metal oxide. Alternatively or in addition, the peptide may be expressed on a portion of the same coat protein (e.g., pVIII) on which the peptide for the metal oxide is expressed. In some embodiments, biopanning using a library of variations in one coat protein is used to identify a peptide sequence for which a polynucleotide is engineered such that the peptide is expressed in a different coat protein.

This is not to say that peptide sequences selective for the metal oxide and the electronic conductor are expressed on the very same protein molecule, rather that both peptides show up in the region of the virus where the particular coat protein is found. For example, some copies of the pVIII protein may include a peptide selective for the electronic conductor, while others include a peptide selective for the metal oxide. Techniques for expressing two separate engineered peptide sequences on the same virus are discussed in Nam, et al., *Nanoletters*, 2004, Vol. 4(1):23-27, the entire contents of which are incorporated herein by reference. Briefly, a phagemid system (Kay, et al., *Phage Display of Peptides and Proteins: A laboratory Manual*; Academic Press: San Diego, 1996, the entire contents of which are incorporated herein by reference), is employed, using a plasmid separate from the already engineered-M13 plasmid to express the catalyst-selective peptide-coat protein fusion. The DNA from the phagemid are packaged into viruses as well as the engineered-M13 plasmid, allowing further copies of the virus to be reproduced later if desired. In some embodiments, at most about 20-30% of the major coat proteins or between zero and five copies of the minor coat proteins such as pIX exhibit the catalyst-selective peptide sequence.

The resulting virus, expressing either one type or two types of modified peptides, may then be used to nucleate nanoparticles of the metal oxide, with or without an electronic conductor. Nanoparticles and nanotubules may be produced at room temperature, in contrast to the elevated temperatures (>150° C.) required for some prior art techniques. In one embodiment, the pVIII-engineered M13 virus is incubated with a metal salt precursor, for example, cobalt chloride, at a concentration between about 1 mM and about 5 mM. Metal ions in solution are chelated by the carboxylic acid ligands. Chelated metal ions are then oxidized by adding a basic solution such as sodium hydroxide (NaOH), at, for example, between about 10 mM and about 100 mM. Alternatively, metallic nanoparticles may be nucleated and grown on the virus major coat proteins by adding between about 5 mM and about 10 mM of a reducing agent such as sodium borohydride ($NaBH_4$) or hydrazine ($N_2H_2$) to a metal salt solution in which the virus is suspended. The virus is fully coated with nanoparticles, forming a metallic nanotube. Because the metallic materials in nanostructures are very reactive, the metallic nanotube is easily oxidized in an aqueous solution or in air to produce a nanotube composed of crystalline metal oxide nanoparticles. In another embodiment, the virus scaffold may be removed from the nanotubes, for example, using enzymes or solvents that disrupt or lyse the viral proteins without disturbing the ceramic phase.

The production conditions may be altered to modify the nanostructure of the oxide nanoparticles. The size of the nanoparticles varies roughly with temperature. Smaller particles may be produced by decreasing the temperature while larger particles may be produced by increasing temperature. The viral system is stable from about 4° C. to about 80° C.; other templates, e.g., peptides, nucleic acids, etc., will be stable in different temperature ranges. Particles may range in diameter from about 2 nm across to about a micron across, for example, between 2 nm and 100 nm, between 100 nm and 500 nm, or between 500 nm and 1000 nm.

The same chemistry may be employed to chelate the electronic conductor to the engineered virus, simply by using a salt of the electronic conductor to the solution in which the metal ion is attached to the virus or using a separate solution. The electronic conductor may be reduced if necessary. Alternatively or in addition, the virus may be incubated with a colloidal solution of nanoparticles of the electronic conductor. Regardless of the proportion of the appropriate peptide in the virus, the proportion of the electronic conductor to the transition metal oxide may be adjusted by adjusting the concentration of the conductor or its salt in solution or modifying the incubation time.

In either embodiment, the diameter of the nanotubes may be adjusted by manipulating the amount of carboxylated amino acids expressed on the coat protein and/or the molar ratio of the metallic ion precursor to the basic reactant or reduction agent. This ratio also determines the uniformity, size and crystal structure of the nanoparticles on these nanotubes.

In another embodiment, alternative metal oxides, such as $Mn_2O_4$ or $V_2O_5$, may formed into nanotubes using the techniques described herein. Other metals that may be used to produce nanotubes according to embodiments of the invention include transition metals, for example, nickel, iron, cadmium, tungsten, chromium, zirconium, titanium, scandium, yttrium, copper, etc. In some embodiments, non-transition metal oxides may be formed into nanotubes. Exemplary metals that may be exploited for use with the invention include but are not limited to calcium, aluminum, barium, beryllium, magnesium, and strontium. All of these may be produced using the same engineered viruses, or biopanning may be employed to identify peptides that are even more selective for the particular metal or metal oxide. Alternatively or in addition, mixed metal oxides may be produced by incubating engineered phage in solutions including salts of more than one metal.

FIG. 1 shows transmission electron microscopy images of $Co_3O_4$ nanotubes grown on an M13 virus scaffold at room temperature according to Example 1. As shown in this figure, regular oxide nanoparticles are uniformly coated on M13 virus, resulting in metal oxide nanotubes. The electron diffraction pattern indicates that the oxide phase is $Co_3O_4$. Nanotubes produced according to certain embodiments of the invention may be as small as 2-3 nm. An exemplary sample of $Co_3O_4$ nanotubes exhibited a surface area of about 140 $m^2$/g. In contrast, cobalt oxide particles formed without any virus or with wild type M13 virus are irregularly shaped and significantly larger than the nanotubes and include a mixture of Co, CoO, and $Co_3O_4$.

Self-Assembly of Nanotubes into a Mesoporous Thin Film

The nanotubes described above may be cast as thin films ranging from about 10 nanometers to about 100 microns, for example, between about 10 nm and about 100 nm, between about 100 nm and about 1 micron, between about 1 micron and about 10 micron, or between about 10 micron and about 100 micron. for use in lithium-ion batteries. U.S. Patent Publication No. 20030073104, the contents of which are incorporated herein by reference, provides exemplary methods of casting films. Films may be cast by simply allowing a solution of the virus to dry, leaving the viral film behind. Films may have a thickness from about 1 micron to about 100 microns, which may be controlled by using a larger or smaller amount of viral suspension in a given area. The nanotubes may exhibit short- or long-range order in the films, for example, as a liquid crystal phase, depending on the concentration of phage in the original solution. In some embodiments, between about $10^{14}$ phage/mL to about $10^{14}$ phage/microliter solutions are employed. The degree of order increases with concentration. M13 bacteriophage exhibits long-range order in liquid crystalline phases due to its unique anisotropic and monodisperse characteristics. Previously, Belcher, et al., have shown that pIII engineered virus suspended in ZnS precursor solution to form viral ZnS nanocrystals contained liquid crystalline suspensions. (8) Although ZnS nanocrystals are linked to pIII proteins at one end of the virus, the long, rod-shaped virus retains its liquid crystalline behavior and can be cast into virus-based thin films with controlled thickness.

Depending on the solvent, the virus concentration, the ionic strength of the solution and, for cobalt oxide and other magnetic materials, the applied external magnetic field, various liquid crystalline phases such as smectic, cholesteric and nematic phases can be achieved. Lower concentrations result in a nematic phase, while progressively higher concentrations result in cholesteric and smectic phases. When the concentration of the virus-based nanotubes in the solution is lower than the critical concentration to form the nematic phase, the nanotubes will not form a liquid crystal phase in cast films. The particular liquid crystalline phase of a nanotube solution will affect the mesoporosity, mesostructure and the mechanical properties of films cast from the solution. All these parameters influence the capacity, lifespan, energy density, and stability of virus-based thin film electrodes.

In some embodiments, it is not necessary that the nanotubes assemble into liquid crystals. Cast films of randomly oriented nanotubes can still exhibit the surface area and mechanical properties needed to produce robust, efficient batteries. Nanotubes fabricated by specific nucleation on engineered virus spontaneously evolve into a self-supported hybrid mesoporous thin film. The spacing between nanotubes, microstructure, and thickness of the film can be regulated by the casting conditions, such as concentration, temperature, pressure and magnetic field. In an alternative embodiment, engineered virus is first cast as a film and then metallized. The film is suspended in solution as described above and a metal or metal nanoparticles chelated to the virus and then oxidized. The cohesion of phage may prevent the film from dissolving in the solution. The film may be arbitrarily thick so long as it does not interfere with the transfer of electrons to and from the ionic charge carriers and across the multiple cells of a battery. One skilled in the art will recognize that the thickness of the film may be optimized to maintain the physical integrity of the film without excessively increasing the internal resistance of batteries incorporating the film.

In an alternative embodiment, the engineered virus are assembled into a film before coordinating the metal oxide and any conductor to the virus. In this embodiment, the film is cast using a solution of the virus, following which the film is processed under the same conditions as the virus to bind the electron conductor and form the metal oxide. Gentle agitation may be used to maintain the uniformity of solutions in which the film is immersed to improve reaction times.

Use of Thin Films

As discussed above, viral films produced according to an embodiment of the invention may be employed in batteries. Li-ion batteries often employ a graphite anode, a liquid or polymer electrolyte, and a cathode that can accumulate lithium ions, such as a transition metal oxide, e.g, cobalt oxide, vanadium oxide, or nickel oxide. In prior art batteries, the lithium ions intercalate themselves between oxide layers. The metal oxide films produced according to various embodiments of the present invention may also accumulate lithium ions through intercalation. As described above, the mobility of the particles within the film allows the film to accumulate and discharge lithium ions without cracking. Without being limited by any particular hypothesis, it is also thought that the lithium ions are additionally accumulated by the film via deposition of lithium oxide on the surfaces of the nanotubes through standard electrochemical mechanisms, e.g., through the oxidation of lithium and the reduction of cobalt or other oxidized metals in the films. The high surface area of the nanotubes within the film provides additional reaction sites for lithium ions, thereby increasing the capacity of an electrode including the film.

One skilled in the art will also recognize that thin films according to an embodiment of the invention may also be employed in the anode of Li-ion batteries. The composition of the particular metal oxide may be selected with reference to the electrochemical potential of the material used at the cathode, whether it is another virus based thin film or some other material. In general, the materials for the anode and cathode of the battery are selected such that, when the battery is discharging, the oxidation of lithium at the anode and its reduction at the cathode is energetically favored, while the reverse reactions are energetically favored during recharging. Any of the transition metal and non-transition metal oxides described above may be used to form films for use on the anode side of a lithium ion battery. Some exemplary materials include cobalt, nickel, chromium, and manganese. Of course, the anode and cathode materials may be optimized with respect to one another to achieve a desired difference in redox potential between the two sides of the cell.

Whether or not the virus-based films exhibit short- or long-range order (or none), they also exhibit mesoporosity defined by gaps between regions of more densely packed virus. This mesoporous microstructure can improve the energy capacity of a battery. A large surface area in the inner and outer walls of virus-based nanotubes may facilitate lithium deposition and intercalation, increasing the capacity of the battery without requiring an increase in size. Moreover, the mesopores can serve as electrolyte channels for faster transportation of the lithium ions to the interior surfaces of the electrode, improving the kinetics of both charging and discharging and reducing the internal resistance of a battery employing the film. In fact, effective uptake and release of cations by oxide nanotubes was investigated and intercalation of lithium ions in high capacity nanotubes was reported (3). The interface between nanotubes in the virus-based film may also act as an intercalation site. These unique characteristics of this mesoporous film can greatly improve the battery capacity.

Thin films produced according to an embodiment of the invention may be used with batteries incorporating both solid electrolytes and liquid electrolytes. The flexibility and high surface area/volume ratio of the films may also facilitate the production of smaller batteries in different configurations. The films may be produced in various shapes, such as cylinder, disc, prism and belt. Alternatively or in addition, thin films according to an embodiment of the invention may be coated onto electrode materials such as platinum, silver, or copper, which materials may be used to conduct current to the thin films from another part of a circuit. The electrode material substrate may be solid or a mesh, especially where a conductive material is included in the film. The virus-based thin film electrode is flexible and ductile and exhibits high capacity and specific energy density. Despite the continuing miniaturization of cell phones and laptop computers, the largest and heaviest component of portable devices continues to be their batteries. Thin films according to an embodiment of the invention may be used to create smaller, more flexible, lighter batteries for smaller devices.

Two purposes served by the electrodes in a battery are electron conduction and providing a site for the oxidation or reduction of the ionic charge carrier (e.g., lithium). Where nanotubes are produced incorporating both oxides and electron conductors, the film may be cast on a more traditional electrode material (e.g., graphite) for use as a solid electrolyte interface layer or may themselves be used as the electrodes. It may be desirable to use metallic leads to connect the various cells in the battery.

Use of Peptides to Create Li-Ion Batteries

In another embodiment, peptides unconnected from viruses may be used to produce metal oxide layers for use in batteries. For example, carboxylated peptide sequences may be immobilized as a monolayer on an electrode material and used to support the formation of a metal oxide layer. In one embodiment, the carboxylated peptide is coupled to an alkanethiol or a polycysteine peptide. Thiolated molecules readily attach to many metals, including gold and nickel. See Whitesides, Proceedings of the Robert A. Welch Foundation 39th Conference On Chemical Research Nanophase Chemistry, Houston, Tex., pages 109-121 (1995). Alternatively, peptides including the carboxylated sequence and a sequence that selectively binds the desired substrate be used to coat an electrode material. Some exemplary sequences that are selective for particular substrates have been reported, for example, in Sarikaya, et al., *Nature Materials*, (2003) Vol. 2, pp 577-585, the entire contents of which are incorporated herein by reference. Others may be identified using the biopanning techniques described above.

In another embodiment, free peptides may be used to form metal oxide nanoparticles. For example, peptides may be synthesized using Fmoc-based solid phase synthesis and electrochemical techniques may be used to form metal oxide nanoparticles whose structure is regulated by the peptides. In one embodiment, an electrochemical cell is constructed using the material whose oxide is being formed as the anode and cathode in anolyte and catholyte compartments separated from the electrolyte by a glass frit. An NaCl solution, for example, about 1M, is used as the electrolyte. The peptide is added to the electrolyte at low concentration, e.g., 10-15 nM. The cell is operated galvanically at low current, e.g., about 10 mA, for a short time, e.g., 1 min to generate metal ions. See Dai, et al., ° Electrochemical and Biomimetic Synthesis and Organization of Hybrid Protein-Inorganic Nanostructures, *JACS*, (2005) 10.1021/ja055499h, the contents of which are incorporated herein by reference.

Figure 2A:
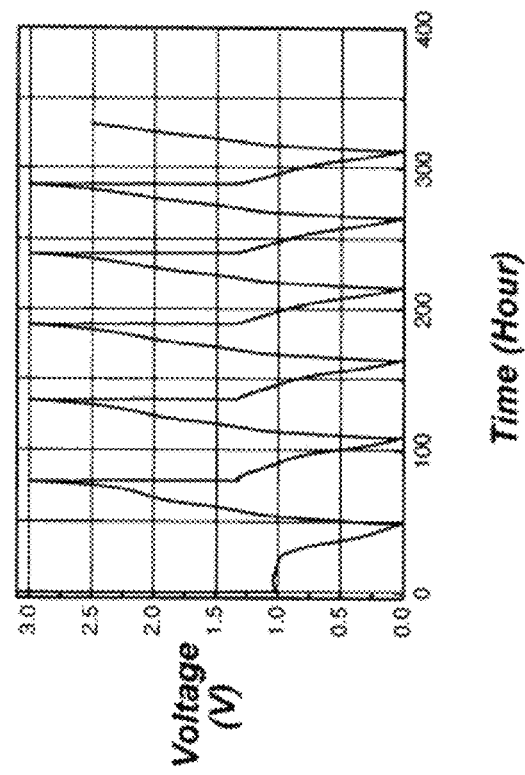
FIG. 2A is a graph showing the variation in specific capacity with cycling of an electrochemical cell including a thin film of cobalt oxide nanoparticles according to an embodiment of the invention.
Figure 2B:
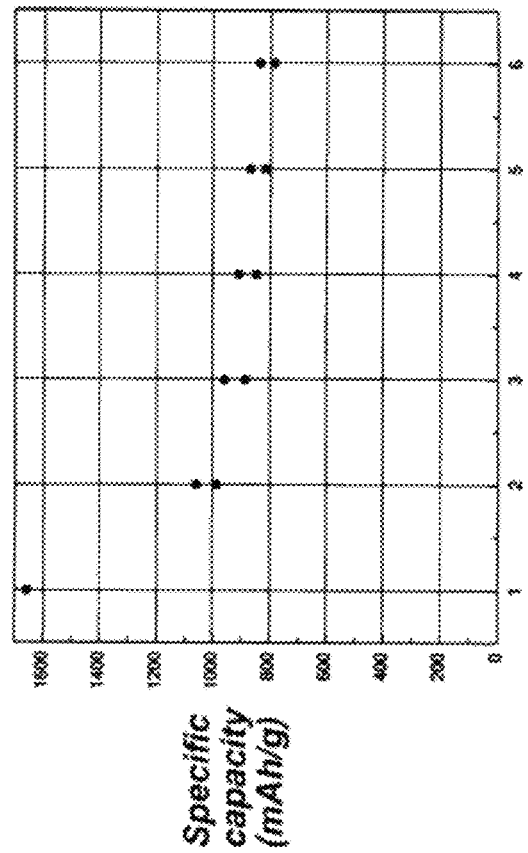
FIG. 2B is a graph showing the variation in voltage with cycling of an electrochemical cell including a thin film of cobalt oxide nanoparticles according to an embodiment of the invention.
Figure 3A:
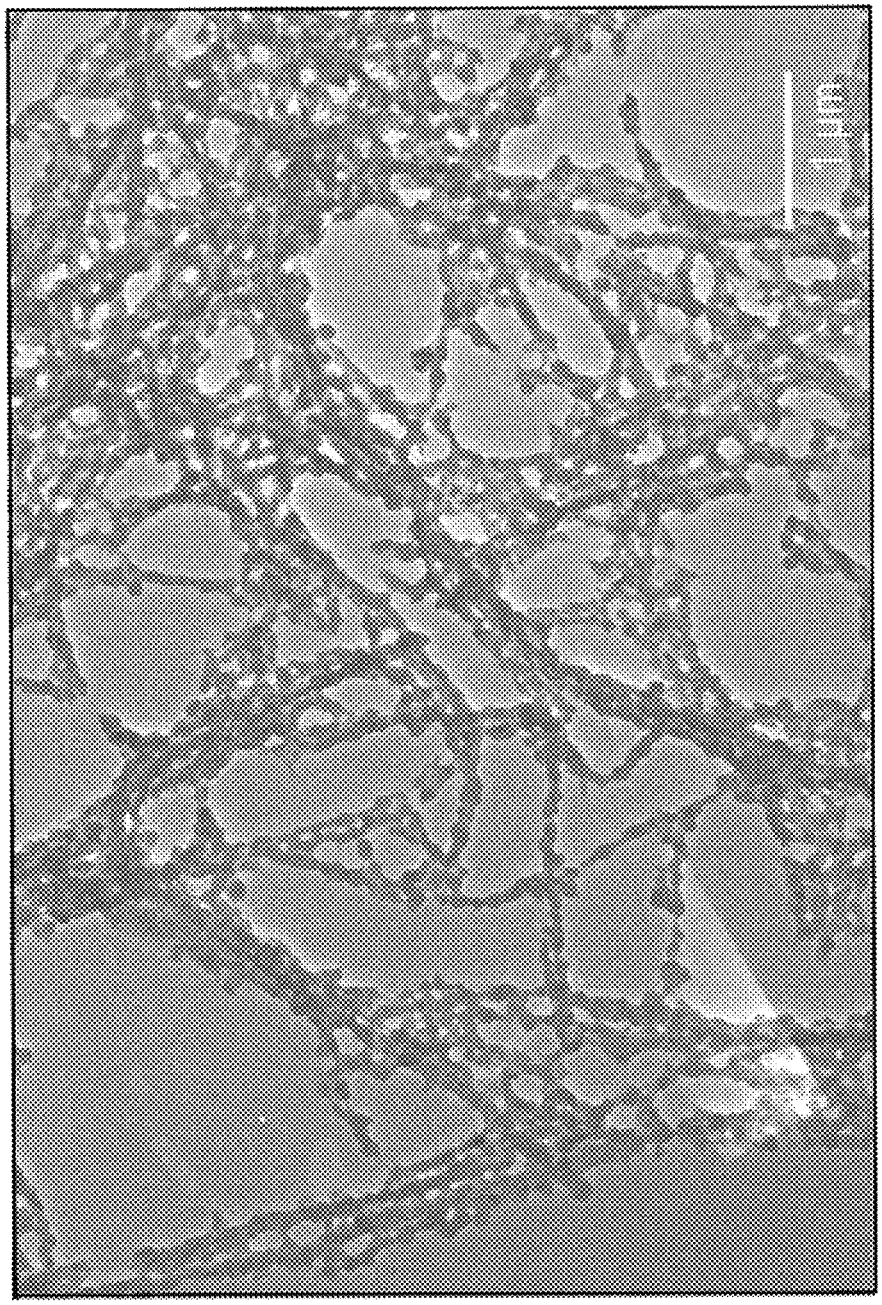
FIG. 3A is a transmission electron micrograph of a thin film of cobalt oxide/gold nanoparticles according to an embodiment of the invention.
Figure 3B:
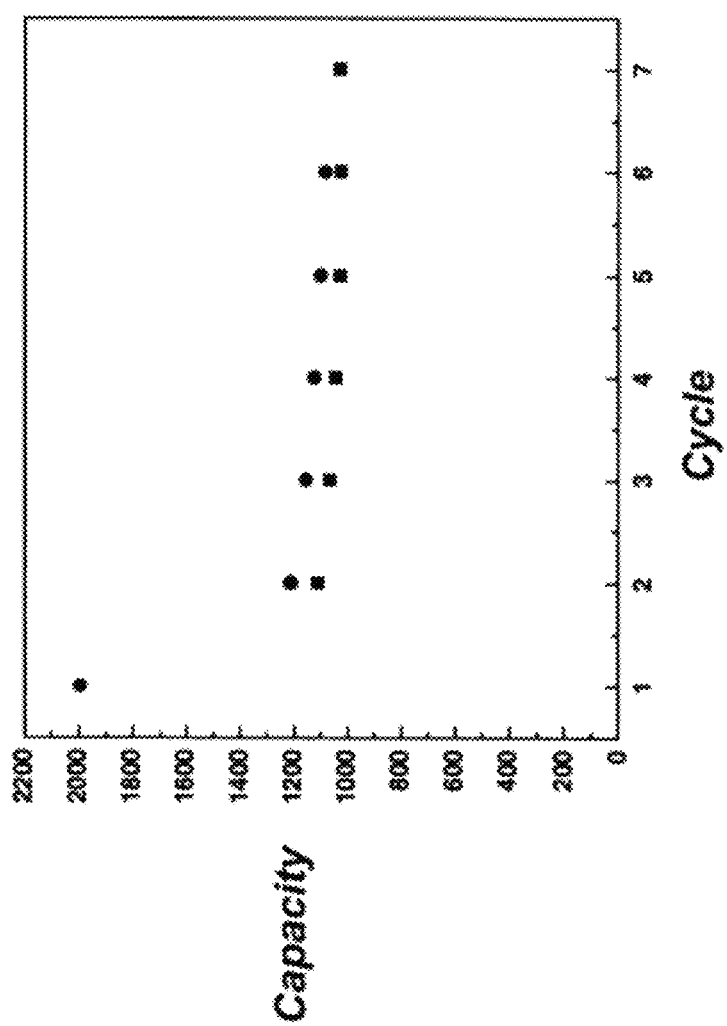
FIG. 3B is a graph showing the variation in specific capacity with cycling of an electrochemical cell including a thin film of cobalt oxide/gold nanoparticles according to an embodiment of the invention.

EXAMPLES $Co_3O_4$ nanotubes were prepared by incubating virus engineered to express sequence E4 in the pVIII coat in an aqueous cobalt chloride solution between 1 and 10 mM at a pH greater than 4, e.g., pH 6, for 30 min at room temperature to chelate cobalt ions to the carboxylated peptide fusions. Sodium borohydride was used to reduce the cobalt ions to cobalt metal, which oxidized spontaneously in water to form monodisperse, crystalline cobalt oxide nanotubes. The nanotubes were formed into films and disposed on platinum electrodes. The electrode was used to prepare a Li ion battery using a lithium metal foil was employed as the anode. A Celgard™ 2400 film saturated with 1M $LiPF_6$ in ethylene carbonate and dimethyl carbonate (1:1 by volume) was used as the electrolyte. The battery was cycled between 3 and 0.01V using MACCOR automated test equipment. The capacity of the battery and the voltage delivered by the battery are shown in FIGS. 2A and 2B Nanotubes incorporating both cobalt oxide and gold were prepared by displaying a gold binding peptide (LKAHLPPSRLPS) (SEQ ID:2) on the E4 phage using a phagemid system. The gold binding peptide was present in about 20% of the pVIII proteins of the E4 phage. A solution of 5 nm gold particles was obtained from Ted Pella and incubated with the engineered virus for about two hours. The phage were then processed as above to produce gold-cobalt oxide nanotubes. The phage were cast into films from a $10^{14}$ phage/mL solution and formed into batteries as described above. A TEM micrograph of the resulting film is shown in FIG. 3A. The variation in capacity with cycling for a Li-ion cell incorporating the film is plotted in FIG. 3B.

REFERENCES

1) J.-M. Tarascon and M. Armand, "Issue and challenges facing rechargeable lithium batteries", *Nature* 414, 359-367 (2001).
2) G. Che, B. B. Lakshmi, E. R. Fisher and C. R. Martin, "Carbon nanotuble membranes for electrochemical energy storage and production", *Nature* 393, 346-349 (1998).
3) Y. Zhou, L. Cao, F. Zhang, B. He, H. Li, "Lithium insertion into TiO2 nanotube prepared by the hydrothermal process, *J. Electrochem. Soc.* 150, A1246-A1249 (2003).
4) J. R. Dahn, U. Von Sacken, M. W. Juzkow, H. Al-Janaby, "Rechargeable LiNiO2/carbon cells", *J. Electrochem. Soc.* 138, 2207-2211 (1991).
5) G. Yuan, M. V. Yakovleva, W. B. Ebner, "Novel LiNi1-xTix/2Mgx/2O2 compounds as cathode materials for safer lithium-ion batteries", *Electrochem. Solid State Lett.* 1, 117-119 (1998),
6) B. Ammundsen, et al., in *Proc. Int. Symp. Electrochem. Soc.* Vol. 99-24, 57-67 (ECS, Pennington, N.J., 2000).
7) W. Donga, D. R. Rolison, B. Dunn, "Electrochemical properties of high surface area vanadium oxides aerogels", *Electrochem. Solid State Lett.* 3, 457-459 (2000).
8) J. Ni, S.-W. Lee, J. M. White, A. M. Belcher, "Molecular orientation of a ZnS-nanocrystal-modified M13 virus on a silicon substrate", *J. Polym. Sci. part B: Polym. Phys.* 42, 629-635 (2004).
9) C. Mao, et al., *Proc. Natl. Acad. Sci. U.S.A.* 100, 6946 (2003).

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

---

The invention claimed is:

1. A composition comprising:
an oxide of a metal coordinated to a protein at a first binding peptide motif,
wherein
the first binding peptide motif exhibits an affinity for a reduced form of the metal,
the first binding peptide motif comprises the sequence AEEEED (SEQ ID NO: 1),
the first binding peptide motif has a length of 25 or less amino acids, and
the metal is selected from the group consisting of cobalt, vanadium, nickel, manganese, cadmium, tungsten, chromium, zirconium, titanium, scandium, yttrium, copper, calcium, aluminum, barium, beryllium, magnesium, and strontium.

2. The composition of claim 1, wherein the metal oxide is an oxidized metal nanoparticle.

3. The composition of claim 1, wherein the metal oxide can intercalate lithium ions.

4. The composition of claim 1, wherein the first binding peptide motif includes carboxylated amino acids.

5. The composition of claim 1, wherein the protein is part of a virus.

6. The composition of claim 5, further comprising a second peptide that selectively binds a predetermined metal selected from copper, nickel, gold, silver, platinum, and palladium.

7. The composition of claim 6, wherein the second peptide is LKAHLPPSRLPS (SEQ ID NO: 2) and the predetermined metal is gold.

8. The composition of claim 6, further comprising the predetermined metal.

9. The composition of claim 8, wherein the predetermined metal is between about 1% and about 30% of the metal coordinated to a protein coat of the virus.

10. The composition of claim 9, wherein the predetermined metal is between about 15% and about 30% of the metal coordinated to a protein coat of the virus.

11. The composition of claim 6, wherein the protein is a coat protein on the virus, and wherein the coat protein includes the second peptide.

12. The composition of claim 6, wherein the first protein is part of a first predetermined coat protein on the virus, and wherein the second peptide is part of a second predetermined coat protein on the virus.

13. A composition produced by the steps of:
providing a protein including a first binding peptide motif, the first binding peptide motif exhibiting an affinity for metal ions;
coordinating a metal to the first binding peptide motif; and
oxidizing the coordinated metal to form a crystallite of the metal oxide, wherein the first binding peptide motif comprises the sequence AEEEED (SEQ ID NO: 1),
wherein the first binding peptide motif has a length of 25 or less amino acids, and
wherein the metal is selected from the group consisting of cobalt, vanadium, nickel, manganese, cadmium, tungsten, chromium, zirconium, titanium, scandium, yttrium, copper, calcium, aluminum, barium, beryllium, magnesium, and strontium.

14. The composition of claim 13, wherein the crystallite has a size between 2 nm and 1000 nm.

15. The composition of claim 13, wherein the first binding peptide motif includes carboxylated amino acids.

16. The composition of claim 13, wherein the metal comprises cobalt.

17. The composition of claim 1, wherein the metal comprises cobalt.

18. The composition of claim 1, wherein the first binding peptide motif has a length of 12 or less amino acids.

19. The composition of claim 13, wherein the first binding peptide motif has a length of 12 or less amino acids.

20. The composition of claim 1, wherein the metal is selected from the group consisting of cobalt, nickel, manganese, cadmium, titanium, yttrium, copper, and calcium.

* * * * *

SEQUENCE LISTING

```
<160> NUMBER OF SEQ ID NOS: 2

<210> SEQ ID NO 1
<211> LENGTH: 6
<212> TYPE: PRT
<213> ORGANISM: Artificial Sequence
<220> FEATURE:
<223> OTHER INFORMATION: Peptide sequence which binds metal ions

<400> SEQUENCE: 1

Ala Glu Glu Glu Glu Asp
1               5

<210> SEQ ID NO 2
<211> LENGTH: 12
<212> TYPE: PRT
<213> ORGANISM: Artificial Sequence
<220> FEATURE:
<223> OTHER INFORMATION: Peptide sequence which binds gold

<400> SEQUENCE: 2

Leu Lys Ala His Leu Pro Pro Ser Arg Leu Pro Ser
1               5                   10
```